United States Patent [19]

Immel et al.

[11] Patent Number: 5,386,060
[45] Date of Patent: Jan. 31, 1995

[54] PALLADIUM CATALYST AND ITS USE IN THE PREPARATION OF A MIXTURE OF OPTIONALLY SUBSTITUTED CYCLOHEXYLAMINE AND OPRIONALLY SUBSTITUTED DICYCLOHEXYLAMINE

[75] Inventors: Otto Immel; Gerhard Darsow, both of Krefeld; Helmut Waldmann, Leverkusen; Gerd-Michael Petruck, Erkrath, all of Germany

[73] Assignee: Bayer Aktiengesellschaft, Leverkusen, Germany

[21] Appl. No.: 966,127

[22] Filed: Oct. 23, 1992

Related U.S. Application Data

[62] Division of Ser. No. 843,473, Feb. 28, 1992, abandoned.

[30] Foreign Application Priority Data

Mar. 8, 1991 [DE] Germany .............................. 4107395

[51] Int. Cl.⁶ .................. C07C 209/72; C07C 209/60; C07C 209/64
[52] U.S. Cl. ..................................... 564/450; 564/451; 564/457; 564/462
[58] Field of Search ................ 564/450, 451, 457, 462

[56] References Cited

U.S. PATENT DOCUMENTS

| | | | |
|---|---|---|---|
| 2,822,392 | 2/1958 | Illich, Jr. et al. | 564/450 |
| 3,636,108 | 1/1972 | Brake | 564/450 |
| 3,983,072 | 9/1976 | Stephens | 502/302 |
| 4,152,351 | 5/1979 | Drake | 558/454 |
| 4,429,155 | 1/1984 | Goetz et al. | 564/402 |
| 4,738,947 | 4/1988 | Wan et al. | 502/304 |
| 4,952,549 | 8/1990 | Immel et al. | 564/450 |
| 5,214,212 | 5/1993 | Whitman | 564/450 |

FOREIGN PATENT DOCUMENTS

| | | |
|---|---|---|
| 0053818 | 12/1981 | European Pat. Off. . |
| 0100267 | 7/1983 | European Pat. Off. . |
| 0126676 | 5/1984 | European Pat. Off. . |
| 0324983 | 12/1988 | European Pat. Off. . |
| 0351661 | 7/1989 | European Pat. Off. . |
| 0805518 | 5/1951 | Germany . |
| 1106319 | 5/1961 | Germany . |
| 3240286 | 5/1984 | Germany ............................ 564/450 |
| 3809226 | 3/1988 | Germany . |
| 56-111045 | 9/1981 | Japan .................. 502/304 |

OTHER PUBLICATIONS

Chemical Abstracts, vol. 60, p. 425c (1964).
Derwent Japanese (Abstracts) of Ja 6813180, vol. 7, No. 5.
Patent Abstracts of Japan, vol. 11, No. 192, Jun. 19, 1987.
Kirk–Othmer, Encyclopedia of Chemical Technology, 3d Ed., pp. 225 & 232 (1978).

Primary Examiner—Richard L. Raymond
Assistant Examiner—Scott C. Rand
Attorney, Agent, or Firm—Sprung Horn Kramer & Woods

[57] ABSTRACT

A Pd catalyst in which an α- or γ-$Al_2O_3$ as support is first treated with at least one compound of the rare earth metals and with at least one compound of manganese and then with at least one palladium compound is suitable for the preparation of a mixture of optionally substituted cyclohexylamine and optionally substituted dicyclohexylamine by hydrogenation of a correspondingly substituted aniline.

16 Claims, No Drawings

PALLADIUM CATALYST AND ITS USE IN THE PREPARATION OF A MIXTURE OF OPTIONALLY SUBSTITUTED CYCLOHEXYLAMINE AND OPRIONALLY SUBSTITUTED DICYCLOHEXYLAMINE

This application is a division of application Ser. No. 843,478, filed Feb. 28, 1992, now abandoned.

BACKGROUND OF THE INVENTION

1. Field of the Invention

The invention relates to a supported palladium catalyst and a process for the preparation of a mixture of optionally substituted cyclohexylamine and optionally substituted dicyclohexylamine by catalytic hydrogenation of optionally substituted aniline using such a catalyst.

2. Description of the Related Art

It is known to prepare cyclohexylamine by pressure hydrogenation of aniline. Cobalt catalysts which contain a basic addition (GB 969,542) and Raney Cobalt (JP 68/03180) are employed for this hydrogenation. According to U.S. Pat. No. 3,636,108, an alkali-moderated ruthenium catalyst on an inert support material is used for the ring hydrogenation of aromatic amine compounds, $NH_3$ and, if appropriate, a solvent additionally being employed. A further process for the pressure hydrogenation of aniline to cyclohexylamine is described in German Auslegeschrift 1,106,319, in which a ruthenium catalyst is likewise used. In this process, co-formed dicyclohexylamine is added to the starting material again; the process involves considerable losses due to the simultaneous formation of cyclohexane. Finally, EP 53,818 considers supported palladium catalysts to be more favourable than ruthenium catalysts for the pressure hydrogenation of aniline; the catalysts described there contain additions which either originate from a group of basic compounds of the alkali metals, alkaline earth metals and rare earth metals or from another group which includes the metals Fe, Ni, Co, Mn, Zn, Cd and Ag. These catalysts permit the reduction of substituted anilines to the respective cyclohexylamines; however, the respective dicyclohexylamines are completely absent.

In all the described pressure hydrogenation processes of aniline, dicyclohexylamine is formed in addition to cyclohexylamine only as a by-product or not at all. In order to obtain dicyclohexylamine in larger amounts, it is prepared by separate processes. Thus, it can be obtained, for example, by pressure hydrogenation of diphenylamine using a ruthenium-$Al_2O_3$ catalyst (German Auslegeschrift 1,106,319). Dicyclohexylamine is furthermore formed in the reaction of cyclohexanone with cyclohexylamine in the presence of palladium on carbon at a hydrogen pressure of 4 bar (FR 1,333,693). In an involved process, dicyclohexylamine can be obtained from the hydrogenation product of aniline on a nickel catalyst by fractional condensation. A part of the co-formed ammonia is removed from the remaining mixture and the residue is fed back into the reaction again (German Patent Specification 805,518).

A common problem in all processes for the ring hydrogenation of aromatic amines consists in the in some cases considerable formation of cyclohexane as a by-product which is not further utilisable.

There was therefore the desire to develop a new process which is also utilisable on the industrial scaled by which both cyclohexylamine and dicyclohexylamine can be prepared in one reaction step in a desired ratio of amounts, in which the loss due to the undesired formation of cyclohexane is suppressed and in which the working life of the catalyst used is additionally improved.

SUMMARY OF THE INVENTION

Surprisingly, it has now been found that the requirements mentioned can be fulfilled by the use of the supported palladium catalyst characterised in the following, which has an $Al_2O_3$ support which contains a combination of compounds of the rare earth metal (sub-group III of the periodic table of the elements) and of manganese.

The invention therefore relates to a palladium catalyst on an $Al_2O_3$ support, which is characterised in that an $\alpha$- or $\gamma$-$Al_2O_3$ is first treated with at least one compound of the rare earth metals (sub-group III of the periodic table of the elements) and with at least one compound of manganese, the amount of the rare earth metal and of the manganese altogether being 0.05 to 8% by weight, preferably 0.2 to 5% by weight, relative to the total weight of the catalyst, and the weight ratio of rare earth metals and manganese being 5:1 to 1:5, preferably 10:9 to 1:2, and is then treated with an amount of at least one palladium compound such that the palladium content is 0.05-5% by weight, preferably 0.05-4% by weight, particularly preferably 0.1-3% by weight, relative to the total weight of the catalyst.

DETAILED DESCRIPTION OF THE INVENTION

The catalyst according to the invention therefore contains as the support an $Al_2O_3$ which has been treated with compounds of the rare earth metals (sub-group III of the periodic table of the elements) and of manganese. A suitable $Al_2O_3$ is the $\alpha$- or the $\gamma$-modification, particularly preferably the $\gamma$-modification. The support has a content of rare earth metal and manganese of altogether 0.05-8% by weight, preferably 0.2-5% by weight, relative to the total weight of the catalyst. The weight ratio of rare earth metal to manganese is 5:1-1:5, preferably 10:9-1:2. Rare earth metal is understood to mean the elements of sub-group III of the periodic table, such as scandium, yttrium, lanthanum and the lanthanides. Preferably, it is understood to mean yttrium, lanthanum, cerium, praseodymium, neodymium and dysprosium, particularly preferably cerium and lanthanum and very particularly preferably cerium. The cerium can in this case be associated with other lanthanides, for example with lanthanum, praseodymium, neodymium, dysprosium or with yttrium. Such an association is incidentally familiar to the person skilled in the art for all the rare earth metals mentioned.

To prepare the catalyst according to the invention, a procedure can be used in which compounds of the rare earth metal and of manganese are applied to an $\alpha$- or $\gamma$-$Al_2O_3$ in the form of extrudates, pellets or spheres with dimensions of about 2-10 mm, the support treated in this way is heated after drying to 200°–450° C. and then impregnated or sprayed with a solution of a palladium salt, after which a fresh drying phase follows.

The application of rare earth metal compounds and manganese compounds to the catalyst support can be carried out, for example, by mere impregnation or spraying with suitable salts of the rare earth metal and of manganese, after which follows a drying phase and the heating phase at 200°–450° C. mentioned. In this process, the salts of the rare earth metal and of the manganese are converted into compounds adhering firmly to the catalyst support without formation of a spinel occurring. However, the application of compounds of the rare earth metal and of manganese can also be carried out by joint precipitation of a rare earth-/manganese hydroxide mixture from rare earth and manganese salts onto the support using alkali metal hydroxide solution or ammonia and, if desired, subsequent washing-out of the soluble components with water. Possible rare earth and manganese salts are in particular the sulphates, chlorides, acetates and/or nitrates of the elements mentioned.

After the application of the rare earth and manganese compounds and if desired after the precipitation described (and the washing-out of water-soluble compounds associated with it), the support treated in this way is first dried before it is heated to higher temperatures (about 200°–450° C., preferably 250°–430° C.). This heating is carried out in a period of 1–120 hours. During this period, the temperature can be increased from lower to higher values in the range indicated.

After the temperature treatment described, the catalyst support treated with compounds of the rare earth metal and of manganese is impregnated with a solution containing palladium. In this case, a procedure can be used in which the palladium, for example in the form of aqueous solutions of the chloride, nitrate, acetate or of another suitable salt, can be impregnated into or sprayed onto the support, followed by drying. If desired, the palladium salts, such as, for example, Pd acetate, can also be brought into solution in organic solvents such as methanol, methylene chloride, acetonitrile or dioxane and impregnated in this form. However, the support impregnated with palladium salts can also be treated with a solution of the abovementioned basic compound before drying, the palladium precipitating as the oxide or hydroxide. Drying also follows here. Such a catalyst according to the invention is then basically available for use. Preferably, however, it is activated before its use, particularly preferably after arrangement in a hydrogenation reactor, by treatment with hydrogen at a temperature of 150°–350° C. After or before activation, it may be desirable to remove anions such as chloride, nitrate, acetate or others and if desired the cations of the basic compounds used for precipitation by washing with water.

However, it is also possible first to impregnate the catalyst support treated with compounds of the rare earth metal and of manganese with the solution of one of the basic compounds mentioned, then to dry and to apply solutions of palladium salts to the catalyst support pretreated in this way and rendered basic, the precipitation of the palladium in the form of its oxide or hydroxide also being carried out at the moment of impregnation. In this case also, the catalyst is basically ready for use after a final drying, but can preferably be activated with hydrogen at the temperature mentioned in the manner described above.

A catalyst treated with basic compounds to precipitate the palladium as the oxide or hydroxide is basically also ready for use in the presence of the residues of those alkaline compounds. Preferably, however, the water washing described is performed.

The impregnation or the spraying of the $Al_2O_3$ support with the substances mentioned and the washing equipment necessary for this are known to the person skilled in the art; the standardisation of the desired treatment by the choice of the amount and concentration of the solutions of the elements mentioned is also known.

The catalysts according to the invention can be outstandingly employed for the ring hydrogenation of optionally substituted anilines at elevated pressure, the preparation in a controlled manner of dicyclohexylamine in relatively large amounts in addition to the simultaneously formed cyclohexylamine taking place in a particularly surprising manner. The catalysts according to the invention exhibit the long working life necessary for continuous industrial processes compared with a pure supported palladium catalyst prepared with compounds of the rare earth metal and of manganese.

Thus, according to the invention, a process for the preparation of a mixture of optionally substituted cyclohexylamine and optionally substituted dicyclohexylamine by hydrogenation of optionally substituted aniline with hydrogen in the presence of the catalyst described above is possible in which the process is carried out in the range from 150°–300° C., preferably 180°–280° C., particularly preferably 150°–240° C. at a pressure of 50–500 bar, preferably 100–400 bar, particularly preferably 150–350 bar.

The hydrogenation, which proceeds exothermically, can be carried out at a relatively high temperature level, which is of great importance for an industrial energy recovery.

The hydrogenation on the catalysts according to the invention can be performed batchwise or continuously, for industrial purposes preferably continuously; in this case the process is carried out in the liquid phase using a firmly arranged catalyst packing.

The catalyst loading is set at an amount of 0.05–2 kg, preferably 0.1–1 kg, particularly preferably 0.15–0.8 kg of aniline per liter of catalyst per hour. A slight change in the conversion of aniline achieved due to a change in activity of the catalyst in the course of relatively long reaction periods can be compensated by a slight adjustment of the reaction temperature or of the other parameters. These ratios can be monitored by the analysis of the reaction mixture.

Possible starting materials within the meaning of the following reaction equation are aniline and substituted anilines, which are converted to the corresponding cyclohexylamines and dicyclohexylamines:

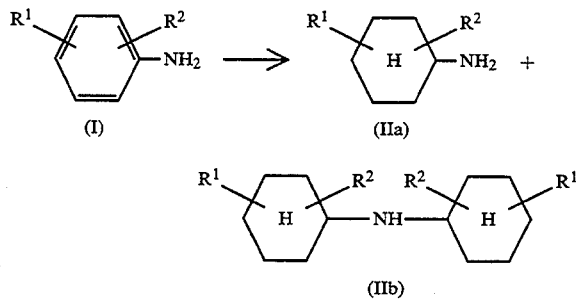

The radicals $R^1$ and $R^2$ independently of one another have the meaning of hydrogen, $C_1$–$C_4$-alkyl or $C_1$–$C_4$-alkoxy. Examples of the alkyl or alkoxy substituents mentioned are: methyl, ethyl, propyl, isopropyl, butyl, isobutyl, methoxy, ethoxy, propoxy, isopropoxy, butoxy or isobutoxy. Preferably, the substituents mentioned have 1–2 C atoms, particularly preferably they are methyl or methoxy. Additionally preferably, one of the substituents $R^1$ and $R^2$ has the meaning hydrogen, while the other substituent denotes alkyl or alkoxy in the context mentioned.

Particulary preferably, the process is directed towards the ring hydrogenation of unsubstituted aniline.

Cyclohexylamines and dicyclohexylamines of the scope of meaning mentioned are used for the preparation of anti-ageing agents for rubbers and plastics, as corrosion inhibitors, and as precursors for plant protection agents and textile auxiliaries.

EXAMPLE 1

200 g of a commercially available $\gamma$-$Al_2O_3$ having a specific surface area of 350 m²/g and a sphere diameter of 2 to 6 mm were impregnated with a solution which had been prepared from 12.4 g of $Ce(NO_3)_3 \cdot 6H_2O$,
18.28 g of $Mn(NO_3)_2 \cdot 4H_2O$ and
75 g of water.

The impregnated $Al_2O_3$ was dried at 120° C. in a water pump vacuum for 18 hours and then kept at a temperature of 400° C. for 3 hours.

100 g of the catalyst support prepared in this way were impregnated with a solution which had been prepared from 4.16 g of Pd acetate and 30 g of dioxane. The catalyst was dried at 100° C. for 18 hours and then activated at 300° C. in a stream of $H_2$ for 3 hours. During the impregnation, 2% by weight of Pd, relative to the total weight of the catalyst, was applied. For hydrogenation of aniline, 60 ml (48.8 g) of the Pd catalyst were placed in a vertically arranged pressure tube (diameter 14 mm, length 70 cm) which was heated using an oil thermostat. For further activation of the catalyst, it was treated at 300° C. and 270 bar of hydrogen for 3 hours. During the course of this, 100 l of hydrogen/h were released.

The temperature was then lowered to about 195° C. and aniline and hydrogen were passed onto the catalyst from above at 280 bar. The liquid trickled downwards over the catalyst into a separator. At the top of the separator, 90 to 100 l/h of hydrogen were released.

The aniline throughput corresponded to a catalyst loading of 0.24 to 0.33 g of aniline/ml of catalyst$\times$h and was kept in this range.

The hydrogenation product was withdrawn from the separator at regular time intervals and analysed. In this way, the following product composition resulted as a function of the running time and of the reaction temperature during an experimental period of more than 1600 hours.

| Running time (h) | Temp. (°C.) | Aniline (%) | DHA* (%) | CHA* (%) | By-products (%) |
|---|---|---|---|---|---|
| 65 | 196 | 0.5 | 84.2 | 15.1 | 0.2 |
| 186 | 194 | 1.2 | 86.4 | 12.0 | 0.4 |
| 474 | 191 | 1.0 | 86.1 | 12.6 | 0.3 |
| 667 | 203 | 0.2 | 84.2 | 15.5 | 0.1 |
| 811 | 203 | 0.1 | 84.2 | 15.6 | 0.1 |
| 909 | 202 | 0.2 | 84.3 | 15.4 | 0.1 |
| 1220 | 204 | 0.2 | 83.7 | 16.0 | 0.1 |
| 1621 | 201 | 0.1 | 83.3 | 16.4 | 0.2 |

*DHA = Dicyclohexylamine; CHA = Cyclohexylamine

EXAMPLE 2

100 g of the catalyst support prepared as in Example 1 were impregnated with a solution which had been prepared from 2.08 g of Pd acetate and 30 g of dioxane. The catalyst impregnated with Pd (1%) was dried at 100° C. for 18 hours.

40 ml (34.5.g) of the catalyst prepared in this way were packed into a pressure tube for the continuous hydrogenation of aniline, and the reaction was carried out in the manner described in Example 1. The catalyst was first activated again at 300° C. and 270 bar before the continuous hydrogenation of aniline was begun.

The aniline throughput corresponded to a catalyst loading of 0.25 to 0.41 g of aniline/ml of catalyst$\times$h. 90 to 100 l of hydrogen were released hourly from the pressure separator. The reaction product exhibited the following composition as a function of the hydrogenation temperature and the experimental period:

| Running time (h) | Temp. (°C.) | Aniline (%) | DHA* (%) | CHA* (%) | By-products (%) |
|---|---|---|---|---|---|
| 119 | 205 | 1.1 | 83.4 | 14.8 | 0.7 |
| 286 | 226 | 0.1 | 72.2 | 25.9 | 0.8 |
| 601 | 232 | — | 73.6 | 26.1 | 0.3 |
| 1098 | 231 | 0.9 | 74.2 | 24.6 | 0.3 |
| 1505 | 231 | 1.8 | 76.3 | 21.5 | 0.4 |
| 1892 | 244 | 0.2 | 69.1 | 30.6 | 0.1 |
| 2134 | 239 | 0.6 | 73.1 | 26.2 | 0.1 |

*DHA = Dicyclohexylamine; CHA = Cyclohexylamine

The composition of the reaction product as a function of the hydrogenation temperature shows that even at high temperatures of 240° C., no losses occur due to hydrogenolysis.

What is claimed is:

1. A process for the preparation of a mixture of optionally substituted cyclohexylamine and optionally substituted dicyclohexylamine by hydrogenation of optionally substituted aniline with hydrogen in the presence of a palladium/$Al_2O_3$ supported catalyst, wherein the the reaction is carried out at 150° to 300° C. and 50 to 500 bar, the catalyst having been produced by first treating $\alpha$- or $\gamma$-$Al_2O_3$ with at least one compound of (A) the rare earth metals (subgroup III of the periodic table of the elements or scandium or yttrium) and with at least one compound of (B) manganese, the amount of the metal (A) and of the manganese (B) altogether being 0.05 to 8% by weight, relative to the total weight of the catalyst, and the weight ratio of metal (A) and manganese (B) being 5:1 to 1:5, and then treating the $Al_2O_3$ with an amount of at least one palladium compound such that the Pd content is 0.05 to 5% by weight, relative to the total weight of the catalyst.

2. The process of claim 1, wherein a catalyst loading of 0.05 to 2 kg of aniline per liter of catalyst per hour is set.

3. The process of claim 2, wherein a catalyst loading of 0.1 to 1 kg of aniline per liter of catalyst per hour is set.

4. The process of claim 3, wherein a catalyst loading of 0.15 to 0.8 kg of aniline per liter of catalyst per hour is set.

5. The process of claim 1, wherein an aniline of the formula

is employed in which $R^1$ and $R^2$ independently of one another denote hydrogen, $C_1$–$C_4$-alkyl or $C_1$–$C_4$-alkoxy.

6. The process of claim 5, wherein $R^1$ and $R^2$ independently of one another denote hydrogen, methyl, ethyl, methoxy or ethoxy.

7. The process of claim 6, wherein $R^1$ and $R^2$ independently of one another denote hydrogen, methyl or methoxy.

8. The process of claim 5, wherein one of the substituents $R^1$ and $R^2$ has the meaning hydrogen.

9. The process of claim 8, wherein unsubstituted aniline is employed.

10. The process of claim 1, wherein in the catalyst the amount of the metal (A) and of the manganese (B) is altogether 0.2 to 5% by weight, relative to the total weight of the catalyst.

11. The process of claim 1, wherein in the catalyst the weight ratio of metal (A) and manganese (B) is 10:9 to 1:2.

12. The process of claim 1, wherein the Pd content is 0.05 to 4% by weight, relative to the total weight of the catalyst.

13. The process of claim 1, wherein the Pd content is 0.1 to 3% by weight, relative to the total weight of the catalyst.

14. The process of claim 1, wherein one or more metals from the group consisting of yttrium, lanthanum, cerium, praseodymium, neodymium and dysprosium is (are) employed as the metal (A).

15. The process of claim 1, wherein one or more metals from the groups consisting of cerium and lanthanum is (are) employed as the metal (A).

16. The process of claim 1, wherein cerium is employed as the metal (A).

* * * * *

UNITED STATES PATENT AND TRADEMARK OFFICE
CERTIFICATE OF CORRECTION

PATENT NO. : 5,386,060
DATED : January 31, 1995
INVENTOR(S) : Immel, et al.

It is certified that error appears in the above-indentified patent and that said Letters Patent is hereby corrected as shown below:

Title page, & Col. 1    Title [54]:  Line 4 delete
line 4 & line 5         " OPRIONALLY " and substitute
                        -- OPTIONALLY --

Signed and Sealed this

Second Day of May, 1995

Attest:

BRUCE LEHMAN

Attesting Officer     Commissioner of Patents and Trademarks